US008437526B2

(12) United States Patent
Spahn

(10) Patent No.: US 8,437,526 B2
(45) Date of Patent: May 7, 2013

(54) SYSTEM FOR ADAPTIVELY PROCESSING MEDICAL IMAGE DATA

(75) Inventor: Martin Spahn, Chicago, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1030 days.

(21) Appl. No.: 12/244,294

(22) Filed: Oct. 2, 2008

(65) Prior Publication Data
US 2009/0148023 A1 Jun. 11, 2009

Related U.S. Application Data

(60) Provisional application No. 60/992,511, filed on Dec. 5, 2007.

(51) Int. Cl.
G06K 9/36 (2006.01)
G06K 9/00 (2006.01)
H05G 1/64 (2006.01)

(52) U.S. Cl.
USPC ............ 382/132; 382/130; 382/131; 378/98.8

(58) Field of Classification Search .................. 382/128, 382/131, 132, 173, 181, 190, 194, 195, 325; 378/19, 62, 91, 98, 98.8, 210, 901
See application file for complete search history.

(56) References Cited

U.S. PATENT DOCUMENTS

| 4,922,915 | A  * | 5/1990  | Arnold et al. ................. 382/128 |
| 6,445,767 | B1 * | 9/2002  | Karellas ....................... 378/98.8 |
| 6,895,077 | B2 * | 5/2005  | Karellas et al. .............. 378/98.3 |
| 7,161,154 | B2   | 1/2007  | Nascetti et al. |
| 7,330,531 | B1   | 2/2008  | Karellas |
| 7,342,993 | B2   | 3/2008  | Besson |
| 2001/0028697 | A1 * | 10/2001 | Nahaliel et al. ................. 378/19 |
| 2005/0152588 | A1 * | 7/2005  | Yoshida et al. ............... 382/128 |
| 2006/0002631 | A1 * | 1/2006  | Fu et al. ........................ 382/294 |
| 2006/0138333 | A1   | 6/2006  | Nascetti et al. |
| 2007/0280409 | A1   | 12/2007 | Konno |
| 2008/0056445 | A1   | 3/2008  | Spahn |
| 2008/0056608 | A1   | 3/2008  | Spahn |
| 2008/0118023 | A1   | 5/2008  | Besson |

OTHER PUBLICATIONS

Search report issued in corresponding Chinese Application No. 200910149733.0 filed May 12, 2009.

* cited by examiner

Primary Examiner — Anastasia Midkiff
(74) Attorney, Agent, or Firm — Alexander J Burke

(57) ABSTRACT

A system locally allocates relatively higher and lower spatial resolution areas of a medical X-ray image in response to image spatial resolution requirements of individual sections of a partitioned image. A system processes image data by adaptively varying pixel resolution within a 2D (two Dimensional) X-ray medical image. The system includes an imaging detector comprising a matrix array of detection picture elements having a detector pixel resolution for detecting X-rays passed through patient anatomy. An image data processor determines a first area within a 2D image to be allocated a first pixel resolution and a second area within the 2D image to be allocated a second pixel resolution lower than the first resolution. A combinational processor combines image data of multiple adjacent detection picture elements to provide an individual pixel of the second pixel resolution. A user interface generates data representing a 2D X-ray medical image including the first area having the first pixel resolution and the second area having the second pixel resolution lower than the first resolution.

19 Claims, 7 Drawing Sheets

FIGURE 5
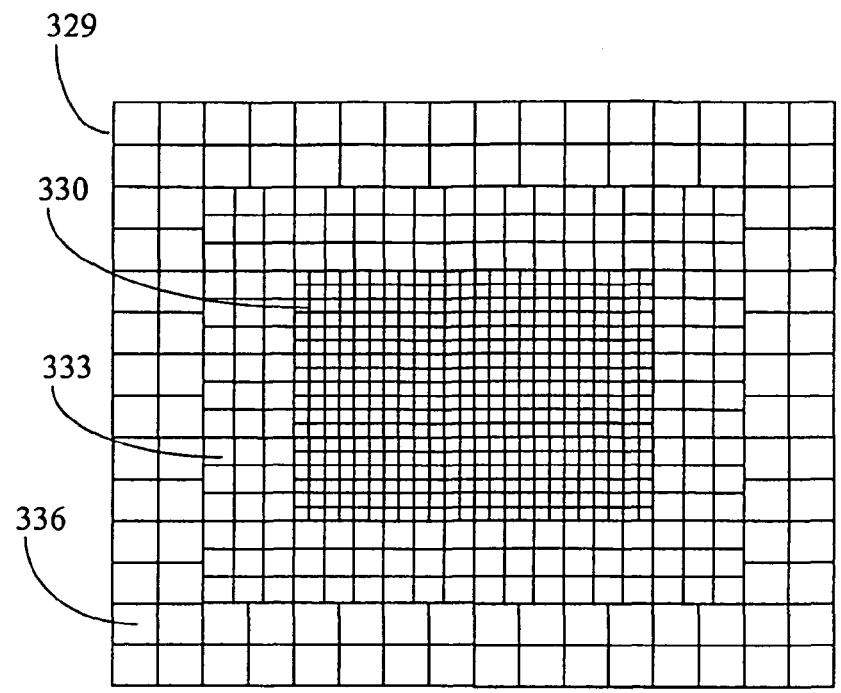
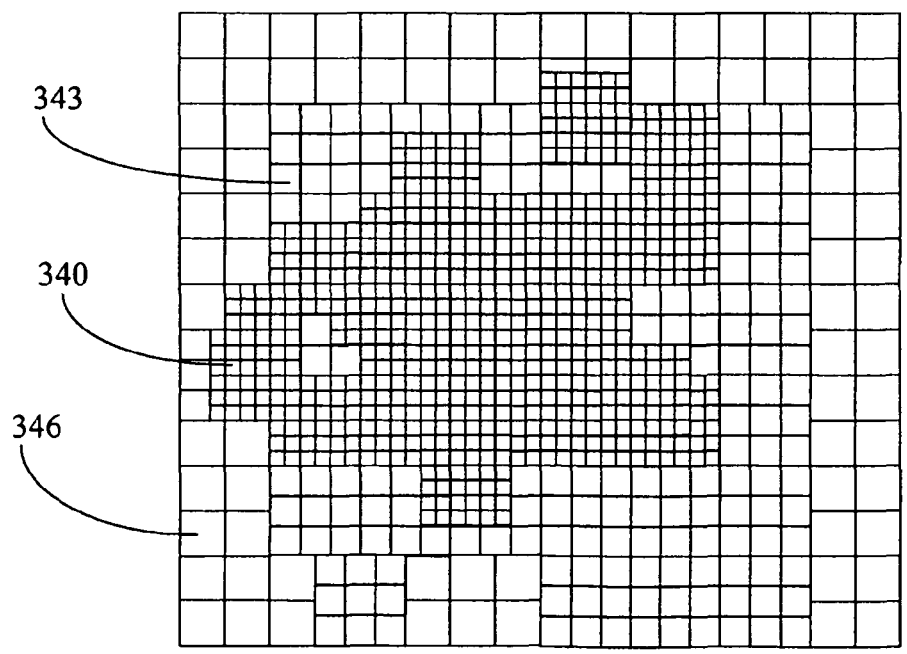
FIGURE 6

SYSTEM FOR ADAPTIVELY PROCESSING MEDICAL IMAGE DATA

This is a non-provisional application of provisional application Ser. No. 60/992,511 filed Dec. 5, 2007, by M. Spahn.

FIELD OF THE INVENTION

This invention concerns a system for processing image data by adaptively varying pixel resolution within a 2D (two Dimensional) X-ray medical image, in response to adaptively determined image (and other) characteristics or predetermined configuration data, for example.

BACKGROUND OF THE INVENTION

Known X-ray systems including real-time X-ray systems providing sequences of medical images for interventional and diagnostic vascular work, or providing individual medical images, use X-ray detectors. The detectors employ an internal physical pixel matrix for acquiring data that may be read out in full pixel resolution or in a reduced pixel resolution. Typically a 2×2 binning step is used to reduce the matrix resolution and hence data size. The data size is reduced to allow use of advanced real-time image processing algorithms and to communicate data across different interfaces having bandwidth limitations. Interface bandwidth limits may arise in different interfaces including within an X-ray detector, between a detector and an image data processing system, within the image data processing system itself and between the image data processing system and a display monitor.

Reduction of spatial resolution is typically performed on image pixel data comprising a complete acquired image even if a zoom function is used to acquire and process only an area of interest to a user. However, reduction of image spatial pixel resolution to provide a reduced quantity of data for processing and communication involves loss of information or image spatial resolution. A system according to invention principles addresses this deficiency and related problems using a smart matrix system avoiding a general loss in image spatial resolution across an image.

SUMMARY OF THE INVENTION

A system locally varies spatial resolution of an image of a medical X-ray diagnostic or interventional system in response to image spatial resolution requirements of individual sections of a partitioned image, determined by an executable application or adaptively locally determined by an image data processor based on local image content of processed image data. A system processes image data by adaptively varying pixel resolution within a 2D (two Dimensional) X-ray medical image. The system includes an imaging detector comprising a matrix array of detection picture elements having a detector pixel resolution for detecting X-rays passed through patient anatomy. An image data processor determines a first area within a 2D image to be allocated a first pixel resolution and a second area within the 2D image to be allocated a second pixel resolution lower than the first resolution. A combinational processor combines image data of multiple adjacent detection picture elements to provide an individual pixel of the second pixel resolution. A user interface generates data representing a 2D X-ray medical image including the first area having the first pixel resolution and the second area having the second pixel resolution lower than the first resolution.

BRIEF DESCRIPTION OF THE DRAWING

FIG. 5 shows an arrangement in which the central part of an X-ray detector array is read out in full image pixel resolution, while outer ring areas are read in successively lower image pixel resolution, according to invention principles.

FIG. 6 shows an arrangement in which the local spatial resolution adaptively determines the combination of local detector picture element data, according to invention principles.

DETAILED DESCRIPTION OF THE INVENTION

Figure 1:
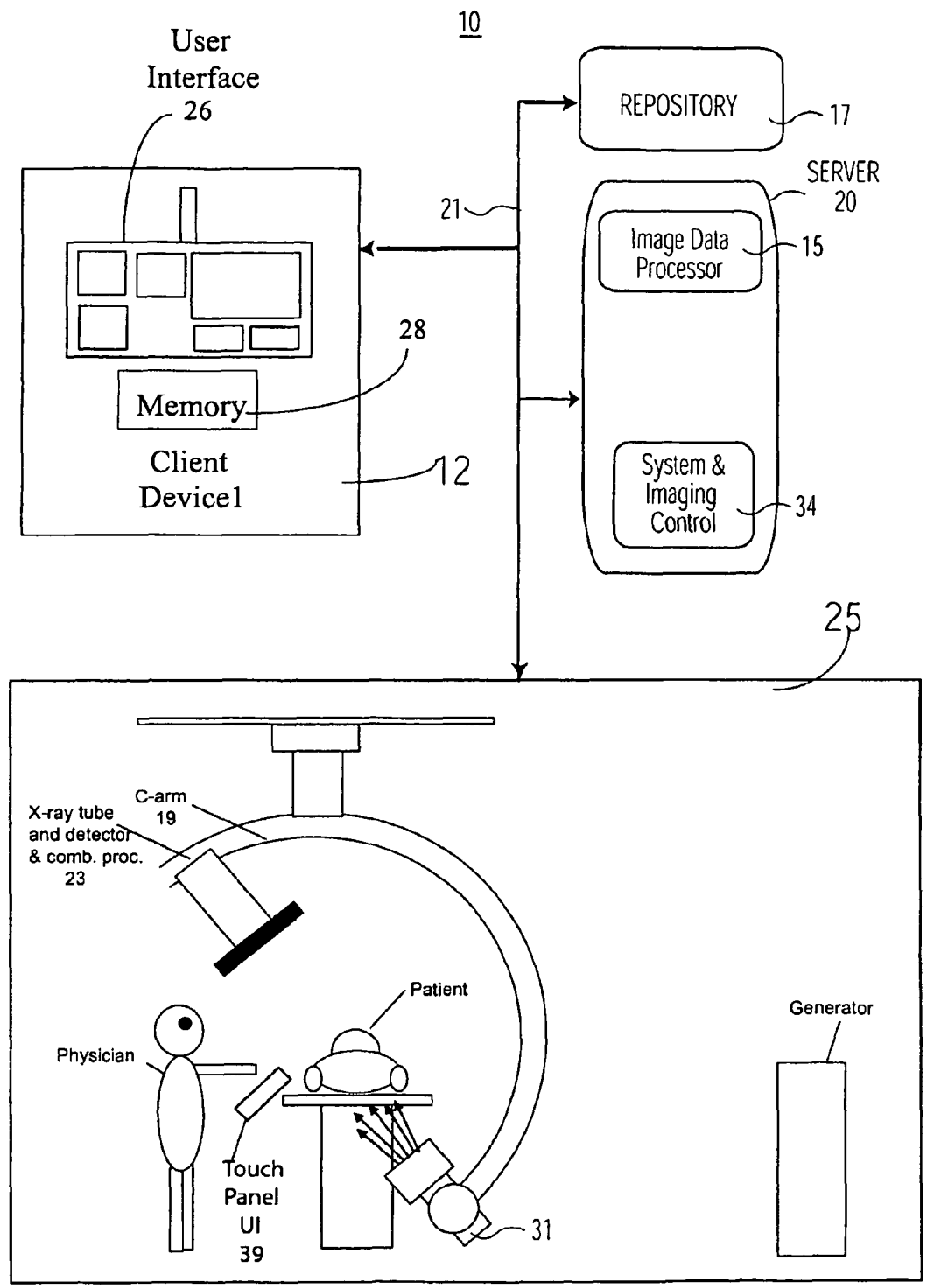
FIG. 1 shows an X-ray imaging configuration including a system for processing image data by adaptively varying pixel resolution within a 2D X-ray medical image, according to invention principles.

A smart matrix system processes image data by adaptively varying pixel resolution within a 2D (two Dimensional) anatomical X-ray medical image. The system advantageously generates a single composite image including one or more image areas having a relatively high pixel resolution compared with pixel resolution of one or more other areas of the image. Thereby, bones, wires and stents, are depicted in relatively high resolution while low contrast image content such as tissue and irradiated areas outside of the patient, for example, that typically do not require high spatial image pixel resolution are depicted in lower pixel resolution. The smart matrix system uses the higher resolution readout processing (e.g., full detector pixel resolution) in high resolution image areas and lower resolution readout processing in lower resolution image areas.

The smart matrix system adaptively varies pixel resolution within a 2D (two Dimensional) anatomical X-ray medical image in response to predetermined configuration data determined by a user or by an executable application, or in response to image content characteristics. Configuration data allocates higher resolution to a center portion of an image for use in cardiac procedure imaging. A cardiac procedure typically requires highest resolution in the center of an image where either vessels need to be seen or interventional objects of high spatial resolution (such as wires, stents, balloons) need to be seen. Outer areas of the image are of lesser interest and do not require the same high pixel resolution. The system adaptively varies pixel resolution within a 2D image in response to image content characteristics using a pixel resolution detection process that determines a pixel resolution best suited to be used for local areas of an image. The smart matrix system advantageously reduces the quantity of image data that needs to be processed and stored enabling use of more complicated and computationally intensive image processing functions on a particular hardware platform and reduction of hardware costs for a particular image processing function.

A processor as used herein is a device for executing stored machine-readable instructions for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a controller or microprocessor, for example. A processor may be electrically coupled with any other processor enabling interaction and/or communication there-between. A processor comprising executable instructions may be electrically coupled by being within stored executable instruction enabling interaction and/or communication with executable instructions comprising another processor. A user interface processor or generator is a known element comprising electronic circuitry or software or a combination of both for generating display images or portions thereof. A user interface comprises one or more display images enabling user interaction with a processor or other device.

An executable application comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A user interface (UI), as used herein, comprises one or more display images, generated by a user interface processor and enabling user interaction with a processor or other device and associated data acquisition and processing functions.

The UI also includes an executable procedure or executable application. The executable procedure or executable application conditions the user interface processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity. An object or data object comprises a grouping of data, executable instructions or a combination of both or an executable procedure.

FIG. 1 shows X-ray imaging system 10 including a system for processing image data by adaptively varying pixel resolution within a 2D X-ray medical image. System 10 includes one or more processing devices (e.g., workstation or portable device such as notebooks, Personal Digital Assistants, phones) 12 that individually include memory 28 and a user interface 26 supporting image presentation in response to user command entered via touch panel 39 and predetermined user (e.g., physician) specific preferences. System 10 also includes at least one repository 17, X-ray imaging modality system 25 (which in an alternative embodiment may comprise an MR (magnetic resonance), CT scan, or Ultra-sound system, for example) and server 20 intercommunicating via network 21. User interface 26 provides data representing display images comprising a Graphical User Interface (GUI) for presentation on processing device 12. At least one repository 17 stores medical image studies for multiple patients in DICOM compatible (or other) data format. A medical image study individually includes multiple image series of a patient anatomical portion which in turn individually include multiple images. Server 20 includes image data processor 15 and system and imaging controller 34.

System 10 acquires data representing multiple temporally sequential individual images of a patient organ using X-ray modality system 25. X-ray modality system 25 comprises C-arm 19 supporting X-ray radiation source 31 and imaging detector device 23 rotating about a patient table. X-ray modality system 25 includes an associated electrical generator for providing electrical power for the X-ray radiation system. Imaging detector 23 comprises a matrix array of detection picture elements having a detector pixel resolution for detecting X-rays provided by source 31 passed through patient anatomy. Image data processor 15 determines a first area within a 2D image to be allocated a first pixel resolution and a second area within the 2D image to be allocated a second pixel resolution lower than the first resolution. A combinational processor in imaging detector 23 (or in another embodiment in image data processor 15) adaptively combines image data of multiple adjacent detection picture elements to provide an individual pixel of the second pixel resolution. User interface 26 generates data representing a 2D X-ray medical image including the first area having the first pixel resolution and the second area having the second pixel resolution lower than the first resolution.

Figure 2:
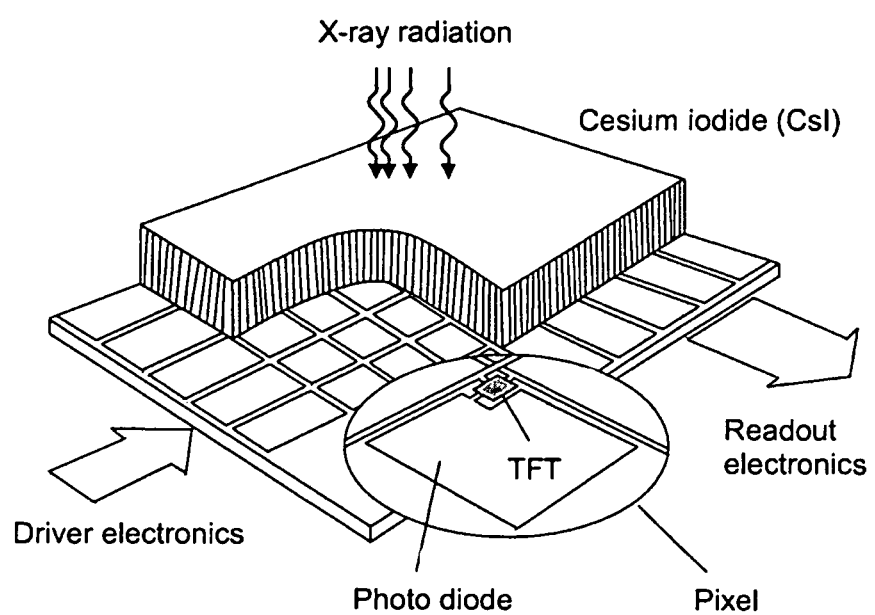
FIG. 2 shows an indirect converting flat detector based on CsI (Cesium Iodide) and an amorphous silicon active readout matrix used in a system according to invention principles.
Figure 3:
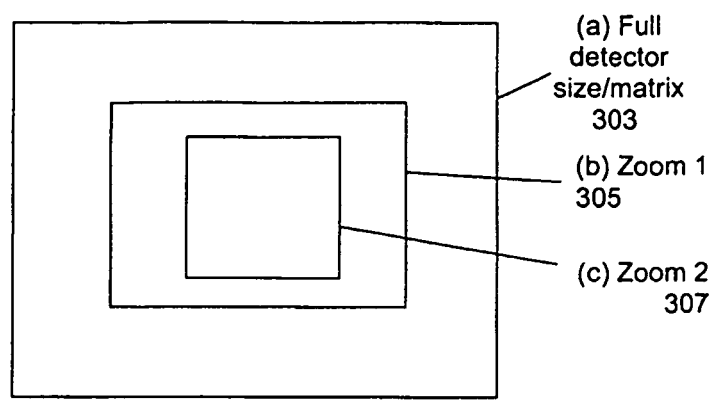
FIG. 3 illustrates different readout areas of a detector, according to invention principles.

FIG. 2 shows an indirect converting flat detector based on CsI (Cesium Iodide) and an amorphous silicon active readout matrix. X-ray radiation is converted by a Cesium Iodide layer to radiation detectable by a matrix array of detection pixel elements comprising photo diodes actively controlled by driver electronics. Electrical signals generated by individual detection pixel element photo diodes are read by detection electronic circuitry used in adaptively varying pixel resolution within a 2D X-ray medical image. Detection electronic circuitry in imaging detector 23 (FIG. 1) adaptively varies pixel resolution in different readout areas of a detector. FIG. 3 illustrates different readout areas having different pixel resolution provided by the Detection electronic circuitry. Specifically, the different readout areas include full area 303 (comprising the complete matrix array of detection picture elements), a first zoom area 305 comprising a reduced picture element readout area with smaller effective matrix array and a second zoom area 307 comprising a further reduced picture element readout area with smaller effective matrix array.

Imaging detector 23 (FIG. 1) may comprise a flat detector based on amorphous silicon and an indirect x-ray converter (Cesium Iodide) or an indirect x-ray converter (Selenium, CdTe, CdZTe, PbO, HgI, etc.). Imaging detector 23 may alternatively comprise an integrating flat detector based on CMOS (complimentary metal oxide semiconductor) structures with direct or indirect x-ray conversion or a counting detector based on CMOS structures with indirect or direct x-ray conversion. Further, some detector-related image processing (like offset, gain, pixel-defect corrections) may be applied before the smart matrix is applied.

In one embodiment, the detection electronic circuitry in imaging detector 23 (FIG. 1) is located close to the detection picture element source inside the detector and adaptively varies the number of adjacent detection picture elements that are combined in this location. This may be performed in analog circuitry or alternatively in digital circuitry or in both (e.g., by partially combining data for some detection picture elements in analog form and combining data for remaining detection picture elements in digital form) to provide an individual pixel of the second pixel resolution. In another embodiment, the detection electronic circuitry in imaging detector 23 (FIG. 1) is located in the image data processing pipeline, for example on an image receiver board (electronic board or computer circuitry with receives the detector pixel data). In a further embodiment, the detection electronic circuitry may be located remote from imaging detector 23 in image data processor 15, for example. The detection electronic circuitry combines data of adjacent detection picture elements in selectable arrays including 1×1 (original, full resolution), 2×2 (4 elements combined to one pixel), 3×3 (9 elements combined to one pixel), n×n or n×m generally, including 1×2, 2×1, 2×3, for example.

Figure 4:
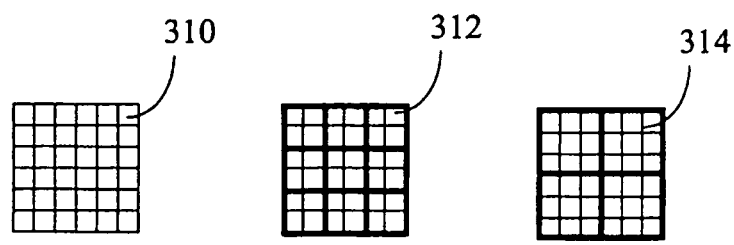
FIG. 4 shows small sections of an active pixel matrix of a flat panel x-ray detector, according to invention principles.

FIG. 4 shows small sections of an active pixel matrix of a flat panel x-ray detector and illustrates how detection picture elements are combined (a process termed binning). A combinational processor in imaging detector 23 (FIG. 1) combines image data of multiple adjacent detection picture elements to provide an individual pixel of a second pixel resolution by combining luminance representative data of adjacent pixels together by averaging (using. 2×2, 3×3 binning). Detection picture element array 310 illustrates full resolution of 36 detection picture elements providing 36 pixels, array 312 illustrates reduced resolution of 36 detection picture elements providing 9 pixels individually comprising averaged 2×2 elements and array 314 illustrates reduced resolution of 36 detection picture elements providing 4 pixels individually comprising averaged 3×3 elements.

FIG. 5 shows an arrangement in which the central part of an X-ray detector array is read out in full image pixel resolution, while outer ring areas are hierarchically read in successively lower image pixel resolution. Specifically, image areas 330, 333 and 336 are respectively allocated predetermined successively reduced image pixel resolution from the image center to the periphery with area 330 having the highest image pixel resolution. Image data processor 15 (FIG. 1) determines first, second and third image areas 330, 333 and 336 respectively, in response to predetermined configuration data identifying first area 330 as a centralized area within 2D image 329 and second area 333 as lying outside first area 330 and third area 336 as lying outside first and second areas 333 and 336.

FIG. 6 shows an arrangement in which local spatial resolution adaptively determines the combination of local detector picture element data (e.g., combination of detector picture element using arrays combining 1×1, 2×2 to 3×3 elements). Pixel resolution of areas within an image is determined image by image by processor 15 (FIG. 1) which detects local luminance (e.g., grey-scale) variation. A seemingly random area 340 corresponding to an X-ray depicted anatomical feature is allocated a first resolution and areas 343 and 346 are allocated predetermined successively reduced image pixel resolution. Image data processor 15 (FIG. 1) adaptively determines image areas 340, 343 and 346 in response to pixel luminance variation within the 2D image. Image data processor 15 adaptively determines image area 340, in response to determining cumulative pixel luminance variation within one or more image areas comprising image area 340 exceed a predetermined threshold and image area 343 is determined at least partially based on lying outside image area 340. Similarly, image data processor 15 adaptively determines image area 343, in response to determining cumulative pixel luminance variation within one or more image areas comprising image area 343 exceed a predetermined threshold and image area 346 is determined at least partially based on lying outside image area 343.

Figure 7:
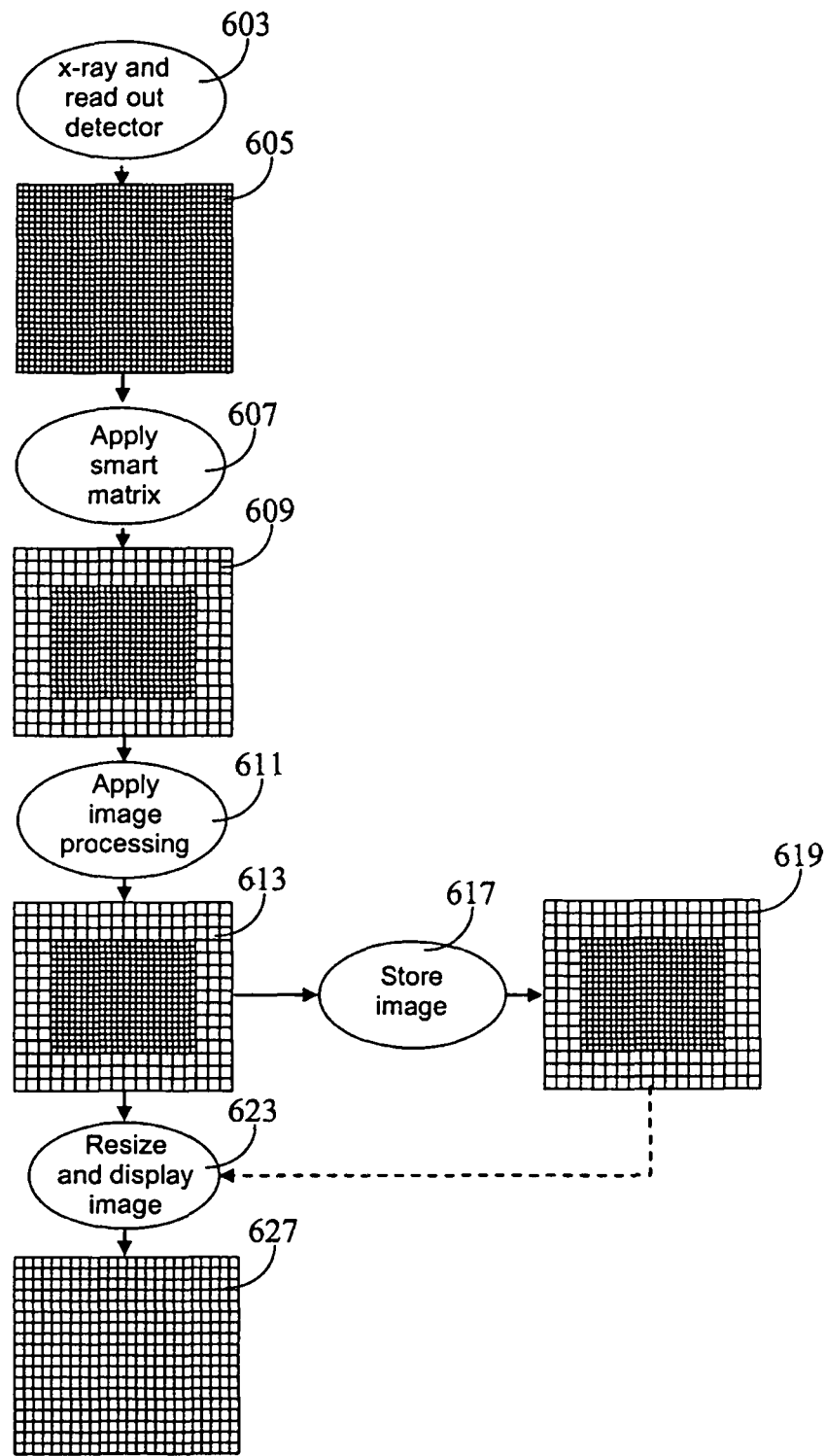
FIG. 7 shows a flowchart of a process of reading and processing data from a physical X-ray detector matrix, according to invention principles.

FIG. 7 shows a flowchart of a process of reading and processing data from a physical X-ray detector matrix 603 comprising an original full resolution detection picture element matrix 605 of a first pixel resolution. X-ray detector matrix 603 is a physical device with regularly arranged detection picture elements. A combinational processor in imaging detector 23 (FIG. 1) (or in another embodiment in image data processor 15) in step 607 adaptively combines image data of a first portion of the multiple adjacent detection picture elements of matrix 605 to provide individual pixels of a second pixel resolution (in image 609). The combinational processor adaptively combines image data of a second portion of the multiple adjacent detection picture elements of matrix 605 to provide individual pixels of a third pixel resolution (in image 609). In step 611, image data processor 15 (FIG. 1) further processes the data representing image 609 (e.g., adjusting the image for contrast, brightness) to provide data representing image 613 for storage in step 617. In step 623, image data processor 15 remaps data representing image 613 or stored data representing image 619 retrieved from storage to be compatible with pixel resolution of a display monitor 627. A portion of the multiple detection picture elements of matrix 605 processed by the combinational processor to provide image 613 or image 619 is remapped to the physical pixel structure of display monitor 627. This is achieved using, bi-linear or cubic interpolation or similar known methods, for example). Image 613 or image 619 may have to be resized as resolution of detection picture elements matrix 605 (and intermediate resolution images 613 and 619) may not match display monitor 627 resolution. The detection picture elements matrix 605 (and intermediate resolution matrix of images 613 and 619) may be a 1500×1800 matrix, in full resolution, while display monitor 627 resolution may comprise 1000×1200 pixels, for example.

Figure 8:
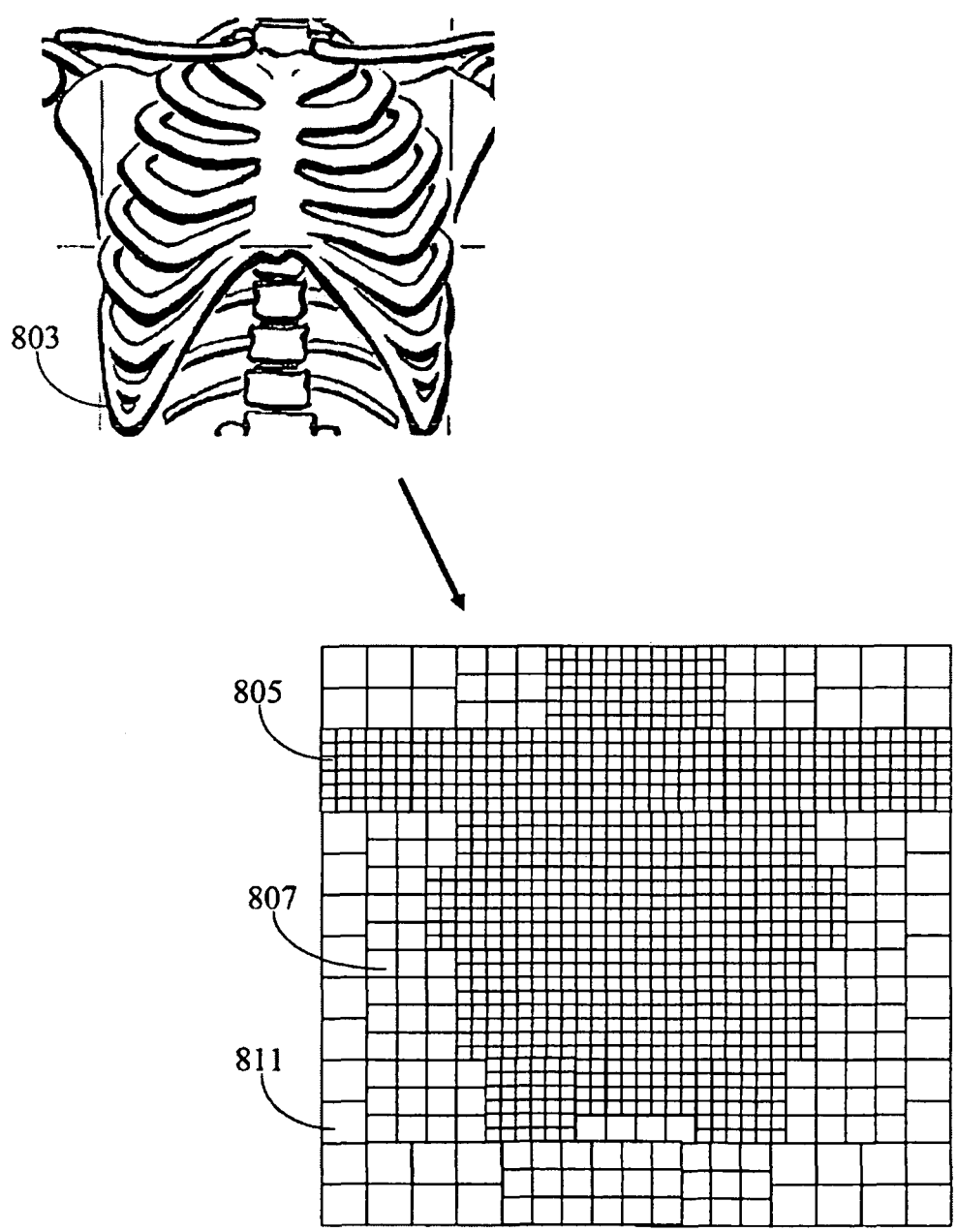
FIG. 8 illustrates smart matrix image data detection of an X-ray image of a thorax, according to invention principles.

FIG. 8 illustrates smart matrix image data detection of an X-ray image of a thorax 803. Image data processor 15 adaptively selects a first area 805 in response to user predetermined anatomical feature selection of a thorax as exemplified by thorax 803. Specifically, image data processor 15 adaptively selects a shape of first area 805 in response to user predetermined anatomical feature (thorax) selection. Image data processor 15 adaptively selects a shape (e.g., a thorax shape) of first area 805 in response to at least one of, (a) a user command and (b) predetermined user preferences. A shape is selected from multiple shapes or patterns pre-stored in repository 17. Selectable shapes or patterns indicate one or more areas and associated pixel resolution and include expected anatomical feature shapes, e.g., thorax 803. Image areas 807 and 811 have successively respectively reduced resolution and lower resolution than area 805. In addition, a shape may be selected from multiple shapes or patterns including, for example, square, rectangular shapes, oval, circular or other predetermined regular or irregular shapes.

Figure 9:
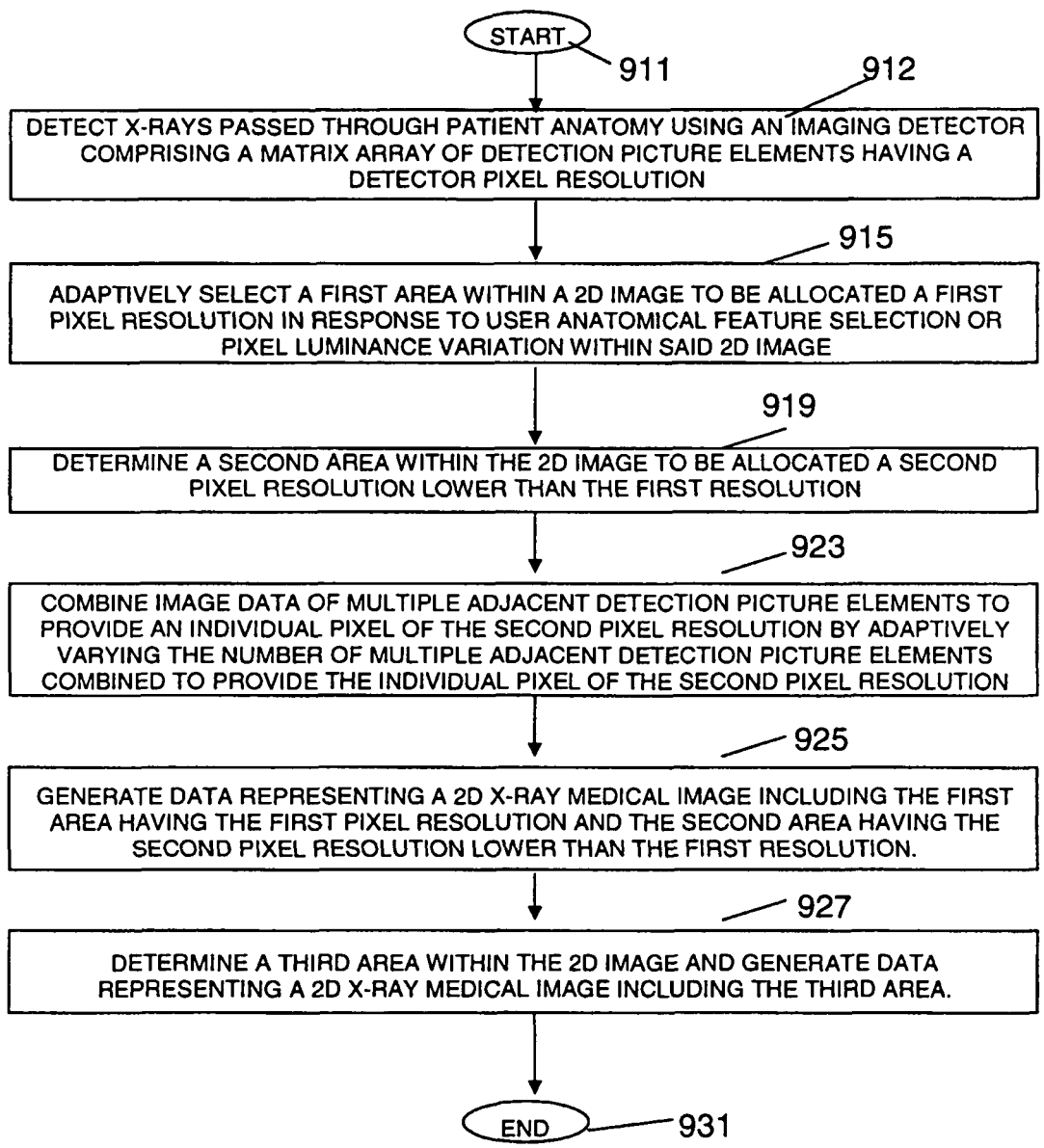
FIG. 9 shows a flowchart of a process for processing image data by adaptively varying pixel resolution within a 2D X-ray medical image, according to invention principles.

FIG. 9 shows a flowchart of a process for processing image data by adaptively varying pixel resolution within a 2D X-ray medical image. In step 912, following the start at step 911, imaging detector 23 (FIG. 1) detects X-rays passed through patient anatomy using an imaging detector comprising a matrix array of detection picture elements having a detector pixel resolution. In step 915, image data processor 15 adaptively selects a first area within a 2D image to be allocated a first pixel resolution in response to user anatomical feature selection or in response to pixel luminance variation within the 2D image and selects a shape of the first area in response to the user anatomical feature selection. Image data processor 15 in step 919 determines a second area within the 2D image to be allocated a second pixel resolution lower than the first resolution. In step 923 a combinational processor in detector 23 combines image data of multiple adjacent detection picture elements to provide an individual pixel of the second pixel resolution by adaptively varying the number of multiple adjacent detection picture elements combined to provide the individual pixel of the second pixel resolution, in response to at least one of, (a) a user command, (b) predetermined user preferences and (c) user predetermined anatomical feature selection. The combinational processor also combines image data of multiple adjacent detection picture elements to provide an individual pixel of the first pixel resolution. In other embodiments, the combinational processor adaptively varies the number of the multiple adjacent detection picture elements combined to provide the individual pixel of the second pixel resolution in response to pixel luminance variation within the 2D image or user anatomical feature selection.

In step 925 user interface 26 generates data representing a 2D X-ray medical image including the first area having the first pixel resolution and the second area having the second pixel resolution lower than the first resolution. In step 927 image data processor 15 determines a third area within the 2D image to be allocated a third pixel resolution and lower than the second resolution and the combinational processor combines image data of multiple adjacent detection picture elements to provide an individual pixel of the third pixel resolution. User interface 26 generates data representing a 2D X-ray medical image including the third area. The process of FIG. 9 terminates at step 931.

The systems and processes of FIGS. 1-9 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. The smart matrix system adaptively varies pixel resolution within a 2D (two Dimensional) anatomical medical image (e.g., an X-ray, MR, CT scan, Ultrasound or other medical image), in response to predetermined configuration data determined by a user or by an executable application, or in response to image content characteristics. The processes and applications may, in alternative embodiments, be located on one or more (e.g., distributed) processing devices accessing a network linking the elements of FIG. 1. Further, any of the functions and steps provided in FIGS. 1-9 may be implemented in hardware, software or a combination of both and may reside on one or more processing devices located at any location of a network linking the elements of FIG. 1 or another linked network, including the Internet.

What is claimed is:

1. A system for processing image data by adaptively varying pixel resolution within a 2D X-ray medical image, comprising:

an imaging detector comprising a matrix array of detection picture elements having a detector pixel resolution for detecting X-rays passed through patient anatomy;

an image data processor for adaptively selecting a first area within a 2D image from a plurality of predetermined regular and irregular shaped areas including a shaped area representing an anatomical organ in response to image content characteristics, said first area being allocated a first pixel resolution and adaptively selecting a second pixel resolution lower than said first resolution to be allocated to a second area within said 2D image, and for allocating an anatomical organ shaped first area said first pixel resolution of higher resolution than said second pixel resolution allocated to said second area lying outside said first area and comprising anatomy outside said organ;

a combinational processor for combining image data of a plurality of adjacent detection picture elements to provide an individual pixel of said second pixel resolution; and a user interface for generating data representing a 2D X-ray medical image including said first area having said first pixel resolution and said second area having said second pixel resolution lower than said first resolution.

2. A system according to claim 1, wherein
a portion of said detection picture elements is remapped to a physical pixel structure of a display monitor to be compatible with pixel resolution of the display monitor and
said image data processor determines said first and second areas in response to image content characteristics comprising an anatomical organ shape.

3. A system according to claim 1, wherein
said image data processor adaptively selects said first area in response to user predetermined anatomical feature selection.

4. A system according to claim 3, wherein
said image data processor adaptively selects a shape of said first area in response to user predetermined anatomical feature selection.

5. A system according to claim 3, wherein
said image data processor adaptively selects a shape of said first area in response to at least one of, (a) a user command and (b) predetermined user preferences.

6. A system according to claim 1, wherein
said image data processor adaptively determines said first area in response to pixel luminance variation within said 2D image.

7. A system according to claim 6, wherein
said image data processor adaptively determines said first area in response to determining cumulative pixel luminance variation within one or more image areas comprising said first area exceeding a predetermined threshold.

8. A system according to claim 7, wherein
said second area is determined at least partially based on lying outside said first area.

9. A system according to claim 1, wherein
said combinational processor combines image data of a plurality of adjacent detection picture elements using interpolation.

10. A system according to claim 1, wherein
said combinational processor adaptively varies the number of said plurality of adjacent detection picture elements combined to provide said individual pixel of said second pixel resolution in response to pixel luminance variation within said 2D image.

11. A system according to claim 1, wherein
said combinational processor adaptively varies the number of said plurality of adjacent detection picture elements combined to provide said individual pixel of said second pixel resolution in response to at least one of, (a) a user command, (b) predetermined user preferences and (c) user predetermined anatomical feature selection.

12. A system according to claim 1, wherein
said combinational processor combines image data of a plurality of adjacent detection picture elements to provide an individual pixel of said first pixel resolution.

13. A system according to claim 1, wherein
said image data processor determines a third area within said 2D image to be allocated a third pixel resolution lower than said second resolution, wherein said combinational processor combines image data of a plurality of adjacent detection picture elements to provide an individual pixel of said third pixel resolution, and
said user interface generates data representing a 2D X-ray medical image including said third area.

14. A method for processing image data by adaptively varying pixel resolution within a 2D X-ray medical image, comprising the steps of:
detecting X-rays passed through patient anatomy using an imaging detector comprising a matrix array of detection picture elements having a detector pixel resolution;
adaptively selecting a first area within a 2D image from a plurality of predetermined regular and irregular shaped areas including a shaped area representing an anatomical organ in response to image content characteristics, said first area being allocated a first pixel resolution in response to user anatomical feature selection;
adaptively selecting a second pixel resolution lower than said first resolution to be allocated to a second area within said 2D image;
allocating an anatomical organ shaped first area said first pixel resolution of higher resolution than said second pixel resolution allocated to said second area lying outside said first area and comprising anatomy outside said organ;
combining image data of a plurality of adjacent detection picture elements to provide an individual pixel of said second pixel resolution by adaptively varying the number of a plurality of adjacent detection picture elements combined to provide said individual pixel of said second pixel resolution; and
generating data representing a 2D X-ray medical image including said first area having said first pixel resolution and said second area having said second pixel resolution lower than said first resolution.

15. A method according to claim 14, including the activities of
selecting a shape of said first area in response to said user anatomical feature selection and
remapping a portion of said detection picture elements to a physical pixel structure of a display monitor to be compatible with pixel resolution of the display monitor.

16. A method according to claim 15, including the activity of
combining image data of a plurality of adjacent detection picture elements in response to said user anatomical feature selection.

17. A method according to claim 16, wherein
said user anatomical feature selection is a predetermined user preference.

18. A method for processing image data by adaptively varying pixel resolution within a 2D X-ray medical image, comprising the steps of:
detecting X-rays passed through patient anatomy using an imaging detector comprising a matrix array of detection picture elements having a detector pixel resolution;
adaptively selecting a first area within a 2D image from a plurality of predetermined regular and irregular shaped areas including a shaped area representing an anatomical organ in response to image content characteristics, said first area being allocated a first pixel resolution in response to pixel luminance variation within said 2D image;
adaptively selecting a second pixel resolution lower than said first resolution to be allocated to a second area within said 2D image;
allocating an anatomical organ shaped first area said first pixel resolution of higher resolution than said second pixel resolution allocated to said second area lying outside said first area and comprising anatomy outside said organ;
combining image data of a plurality of adjacent detection picture elements to provide an individual pixel of said second pixel resolution by adaptively varying the number of a plurality of adjacent detection picture elements combined to provide said individual pixel of said second pixel resolution; and
generating data representing a 2D X-ray medical image including said first area having said first pixel resolution and said second area having said second pixel resolution lower than said first resolution.

19. A method according to claim 18, wherein the activity of adaptively varying the number of said plurality of adjacent detection picture elements combined is performed in response to pixel luminance variation within said 2D image and including the activity of
remapping a portion of said detection picture elements to a physical pixel structure of a display monitor to be compatible with pixel resolution of the display monitor.

\* \* \* \* \*